United States Patent [19]

Forgeot

[11] Patent Number: 5,759,585
[45] Date of Patent: Jun. 2, 1998

[54] PLASMALOGEN COMPOSITIONS AND THEIR USE IN NEURODEGENERATIVE DISEASES TREATMENT

[75] Inventor: Marcel Forgeot, Dampierre-en-Yvelines, France

[73] Assignee: S.AR.L. Institut d'Hygiene et Dietetique, France

[21] Appl. No.: 809,165

[22] PCT Filed: Jul. 2, 1996

[86] PCT No.: PCT/FR96/01028

§ 371 Date: Mar. 4, 1997

§ 102(e) Date: Mar. 4, 1997

[87] PCT Pub. No.: WO97/02828

PCT Pub. Date: Jan. 30, 1997

[30] Foreign Application Priority Data

Jul. 7, 1995 [FR] France ................... 95 08223

[51] Int. Cl.$^6$ ............ A61K 35/30; A01N 57/10; C07C 69/52
[52] U.S. Cl. ............ 424/570; 514/143; 560/205
[58] Field of Search ............ 424/520, 522, 424/523, 572, 574, 570; 514/75, 143, 558, 571, 667, 670, 671, 715, 722, 739; 560/205

[56] References Cited

U.S. PATENT DOCUMENTS 4,613,621 9/1986 Horrmann ................... 514/693

FOREIGN PATENT DOCUMENTS 2721516 12/1995 France .
9321190 10/1993 WIPO .

OTHER PUBLICATIONS

Martinez et al. "Lipids of the developing human retina: I. Total faty acids, plasmalogens and fatty acid composition of ethanolamine and choline phosphoglycerides", J. Neurosci. Res. (1988) 20: 484–490.

Markesbery et al. "Brain trace element concentrations in aging", Neurobiol. Aging (1984) 5: 19–28.

Gurr et al. Lipid Biochemistry: an Introduction. 3rd edition (1980) (Chapman and Hall: London), pp. 4, 5 and 25.

Mitani et al. "Aluminum deficiency in central nervous system (CNS) tissue with a mineral deficiency", Biomed. Res. Trace Elem. (1990) 1(2):149–50 (abstract only).

*Primary Examiner*—Jon P. Weber
*Assistant Examiner*—Susan Hanley
*Attorney, Agent, or Firm*—Bierman, Muserlian and Lucas

[57] ABSTRACT

The present invention is directed to plasmalogens and pharmaceutical compositions thereof which are useful for treating neurodegenerative diseases. Carbons 1 and 2 of the phosphoglyceryl backbone of the plasmaolgens have from 10-24 carbon atoms containing from 1 to 6 double bonds. The phosphoryl group is bonded to choline, ethanolamine, serine or inositol.

7 Claims, No Drawings

PLASMALOGEN COMPOSITIONS AND THEIR USE IN NEURODEGENERATIVE DISEASES TREATMENT

DESCRIPTION OF THE INVENTION

The present invention relates to the field of therapeutic chemistry and more particularly to the one of phosphoglycerids.

More precisely, it consists in pharmaceutical compositions notably intended for neurodegenerative diseases treatment, based on phosphoglyceroethers and phosphoglyceroesters.

STATE OF THE ART

Specifically, it consists in pharmaceutical compositions containing phosphoglyceroethers or plasmalogens, combined or not with phospholipids, admixed or diluted into inert, not toxic carriers, suitable for digestive or parenteral administration.

Phospholipids are defined as esters constituted of a glycerol molecule esterified in position 1 and 2 with saturated or unsaturated fatty acids chains, and, in position 3 with a phosphoric acid derivative. Most of natural phospholipids contains saturated fatty acids chains such as stearic acid or palmitic acid. Moreover, the phosphoric group is bound to an aminoalkyl chain to form the phosphatidylcholine, phosphatidylethanolamine, phosphatidylserine and phosphatidylinositol. These compounds which form the lecithins class are principally of alimentary value.

The phospholipids, according to this invention, are characterized in that the glycerol moiety is esterified and/or etherified by non saturated fatty chains.

Previous tests have shown the relevance of phospholipids containing polyunsaturated fatty acids as an esterifying group.

Their function in nutrition and dietetic has already been the subject to several patent applications depending on whether they origin from cerebral tissues or whether they come from the yolk of hens egg extracts the food of which has been modified.

In fact, these phospholipids are carriers of fatty acids chains with a high number of carbons and they have a high unsaturation degree of the n-3 series, especially the acid in $C_{22}:6$.

The superiority in nutritional function of the cerebral phospholipids in comparison with other sources of n-3 fatty acids has been more particularly demonstrated (J. M. BOURRE J.Neur.Chem. 60 (1993) 2018–2028).

SUMMARY OF THE INVENTION

The present invention thus relates to pharmaceutical compositions in which the phosphoglycerids are, partially or predominantly, substituted by plasmalogens the formula of which is:

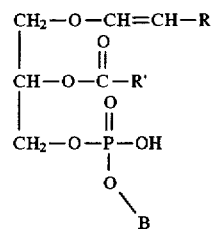

wherein R is an alkyl radical and, preferably, an alkenyl radical having one or several double bonds up to 5 double bonds, and from 10 to 24 carbon atoms R' is a linear or branched, fatty, alkenyl of 10 to 24 carbon atoms and from 1 to 6 double bonds and the nitrogen atom is inserted into a secondary, tertiary or quaternary, linear or cyclic structure.

The Merck Index (1989) page 1194, defines plasmalogens as aldehydogenic lipids extracted from the animal kingdom and nothing is known about their therapeutic usefulness.

Their nomenclature is not already entirely determined and it is spoken as ethanolamine-phosphatidal or plasmalogen-ethanolamine, or plasmalogen-choline to define more precisely the nitrogenous structure carried by the phosphoric group.

Phosphoglycero-ethers of the invention seem to have a high affinity for polyunsaturated fatty acids with a long chain of the n-3 series and it can be deduced therefrom a great physiological significance for eicosanoids. In this case, one characteristic of plasmalogen is that it contains twice more from a polyunsaturated fatty acid (DHA i.e. $C_{22}$: 6 n-3) than other phospholipids.

Plasmalogens molecules are essentially present on the membrane and seem endowed with remarkable membrane exchange qualities. So, they would have a greatest metabolic activity at the level of the membrane reconstruction.

Moreover, it has been shown that cultured mutant cells which do not synthetize plasmalogen are very sensitive to agents generating free radicals (O. MORAND J.Biol.Chem. 263 (1988) 11.797). This leads to suppose a vitamin E-like protective effect of the plasmalogen with a role of anti-oxidizing in the oxidative stresses (B. ENGELMANN Biochem.Biophys.Res.Commun. 204 (1994) 1235).

The relevance of phosphoglycero-ethers appears during various genetic diseases, as well in the animals as in the humans. So, among others, mutant mice breeds, used in laboratory, like "Jimpy" mice and "Quaking" mice have a depressed plasmalogens level, as well in the brain as in the spinal chord (M. H. HACK J.of Chromatogr. 145 (1978) 307), likewise pigs suffering from congenital trembling (D. S. PATTERSON J.Neurochem. 21 (1973) 397).

Besides, in the humans, the Zellweger's cerebrohepatorenal syndrome is a rare genetic disease with a brain degeneracy associated with an etherphospholipids insufficiency due to a lack of peroxisoms which are their biosynthesis sites.

In this disease, a great quantity of phospholipids esters with very long fatty acids chains of the n-6 serie is found in affected children's brain with, simultaneously, a very important decrease in the level of the n-3 series fatty acids, and particularly, of $C_{22}$-6 (DHA) (A. POULOS Biochem.J. 253 (1988) 645).

Some other hereditary diseases induce neurological disorders of demyelinisation with a significant decrease in the level of plasmalogen at the cerebrospinal level, it is such the case of the Pelizaeus-Merzbacher's leukodystrophic disease (J. M. BOURRE Europ.J.Neurol. 17 (1978) 317), as well as in the Refsum infantile disease too, the punctata chondrodysplasia and some others (A. K. HAJRA Plenum Press (1988) 369–380).

Some other degenerative diseases are associated with a perturbation of the phospholipids metabolism and, particularly, of plasmalogen at the cerebrospinal level, it is such the case in multiple sclerosis (J. M. BOGGS Neur.Chem.Res. 7 Août 1982 p.953–954).

In several demyelinisation diseases and in ischemia, a rise of the plasmalogen level in cerebral tissues is observed, that is confirming the role of plasmalogens in myelin (L. A. HORROCK Adv.Exp.Med.Biol. 100 (1978) 423–438).

The degradation of phospholipids membranes seems to be associated with Alzheimer's disease and a lowering of cerebral phosphatidylcholine and phosphatidylethanolamine level (R. M. NIBCH Proc.Natl.Acad.Sci.USA 89 (1992) 1671), and also, a lowering of the rate of polyunsaturated fatty acids and, particularly $C_{22}$: 6 (M. SODERBERZ Lipids 26 (1991) p.421–425) are reported.

Similar modifications of the same order have been reported in the Down's syndrome (B. W. BROOKSBANK Mal.Chem.Neuropathol. 11 (1989) p.157–185).

Preceeding informations have incited applicants to search phospholipidethers sources and to measure their possible protective efficacy towards oxydizing agents or to degenerative processes.

Mammalian brain and spinal chord appear as the best sources of phospholipidethers, in the form of plasmalogens; the used preparation contains about 12% of plasmalogens with a high proportion of polyunsaturated n-3 fatty acids, the composition of which is following:

| sphingomyeline | 5 to 10% |
|---|---|
| phosphatidylcholine | 20 to 30% of which ½₀ is in plasmalogens form |
| phosphatidylserine | 15 to 20% |
| phosphatidylinositol | 3 to 5% |
| phosphatidylethanol-amine | 30 to 40% of which ⅔ are in plasmalogens form |
| phosphatidic acid | 3 to 5% |
| lysophospholipids | 2 to 10% of which total plasmalogens are 10 to 15% |
| fatty acids n-3 total = | 11% |
| ratio n-6/n-3 = | 15% |
| ration $C_{22}$: 6 (n-3)/ fatty acids total) = | 10% |

By comparison, hens eggs fed with a rich feeding of n-3 series fatty acids contain a lower proportion but however significative of plasmalogens as well as a lesser quantity of n-3 serie long chain fatty acids as it is shown in Table I below:

TABLE 1

| HEN EGGS PHOSPHOLIPIDS | | ETHER LIPIDS |
|---|---|---|
| Cholinephosphatidyl | 70% | 0 |
| Phosphatidyl ethanolamine | 16% | 2.8 to 4% |
| Other phospholipids | 12% | 0 |
| Total amount of lipids ethers | | 0.5 to 1% |
| n-3 fatty acids total | 6 to 7% | |
| Ratio n-6/n-3 | 5 to 6% | |
| Ratio $C_{22}$: 6 (n-3)/ Fatty acids total | 5% | |

This is the reason why a cerebral phospholipids preparation rich in plasmalogens (phosphoglycero-ethers) the composition of which and the plasmalogens content seems to be particularly suitable, is preferably used.

In a more particular way, phospholipids used in the present invention contain from 5 to 25% of total plasmalogens and preferably from 10 to 15%.

The compositions, according to this invention, also find a use to fight against intoxications or nervous degeneracies, diseases in which either a deficiency in the biosynthesis or a phospholipids degradation containing an ester link or an ether link with an hydrocarbonated polyunsaturated fatty acid chain, particularly, the one of the n-3 series, can be shown. It results in a more or less reversible damage of the nervous cell membrane wall.

The compositions according to this invention are intended to digestive or parenteral administration. For these aims, there will be added to excipients or diluents suitable for these ways of administration, such as inert mineral products, for example, calcium carbonate, tricalcium phosphate, magnesium phosphate, alumina, colloidal silica, kaolin, clays, aluminium silicate, calcium silicate or iron oxide for the digestive way of administration, of aqueous liquids for the parenteral way of administration.

The compositions according to this invention, can also contain organic inert supports of organic nature such as starches, dextrins, lactose, cellulose, cellulose synthetic derivatives, alginates, carrhagenates, fatty acids, waxes or resins.

The compositions according to this invention can also contain other active agents with complementary action such as the group B vitamins (vitamin B1, vitamin B2, vitamin B6, folic acid, pantothenic acid, pangamic acid, vitamin PP) or mineral salts or trace elements such as selenium, lithium or rubidium.

The compositions according to this invention thus appear in the form of drinkable vials, flasks, soft gelatine capsules, uncoated or coated tablets, lozenges, granules or flavoured or not, sweetened or not powders.

The compositions according to this invention can also appear in the liquid form such as, for example, a gelified preparation or a drinkable suspension or even more an oil in water emulsion.

The present invention is also described with more details in the following examples:

EXAMPLE I

A preparation based on phospholipids rich in ether lipids (plasmalogen) and preferably extracted from mammalians or fishes brains or spinal chord and optionally from hens eggs.

Cerebral phospholipids 10 to 300 mg of which 10 to 15% of ether lipids:

| • Vitamin B1 | 0.30 to 4.2 mg |
|---|---|
| • Vitamin B2 | 0.30 to 4.8 mg |
| • Vitamin B6 | 0.35 to 6 mg |
| • Folic acid | 30 to 600 µg |
| • Vitamin B12 | 0.15 to 3 µg |

For one capsule

EXAMPLE II

Capsules based on cerebral phospholipids rich in ether lipids (plasmalogen)

| • Preparation according to example I | 70.0 g |
|---|---|
| • Lactose | 175.5 g |
| • Vitamin E | 20.0 g |
| • Microcrystalline cellulose | 30.0 g |
| • Calcium stearate | 4.5 g |

For 1000 capsules

EXAMPLE III

Capsules based on cerebral phospholipids rich in ether lipids (plasmalogen)

| | |
|---|---|
| • Preparation according to example I | 65.0 g |
| • Magnesium oxide | 75.0 g |
| • Zinc gluconate | 100.0 g |
| • Maltodextrin | 59.25 g |
| • Colloidal silica | 0.75 g | for 1000 capsules

EXAMPLE IV

Capsules based on cerebral phospholipids rich in ether lipids (plasmalogen)

| | |
|---|---|
| • Preparation according to example I | 90.5 g |
| • Magnesium oxide | 100.0 g |
| • Yeast autolysate titrated in vitamins of the B group | 55.0 g |
| • Carboxymethyl cellulose | 53.6 g |
| • Colloidal silica | 0.9 g | for 1000 capsules

EXAMPLE V

Plasmalogen-based capsules

| | |
|---|---|
| • Preparation according to example I | 100.0 g |
| • Lactose | 770.0 g |
| • Magnesium stearate | 20.0 g |
| • Colloidal silica | 3.0 g | for 1000 capsules

EXAMPLE VI

Tablets based on cerebral phospholipids rich in ether lipids (plasmalogen)

| | |
|---|---|
| • Preparation according to example I | 95.5 g |
| • Magnesium oxide | 250.0 g |
| • Sorbitol | 637.5 g |
| • Microcrystalline cellulose | 15.0 g |
| • Colloidal silica | 2.5 g | for 1000 capsules

EXAMPLE VII

Ampuls to be drunk based on cerebral phospholipids rich in ether lipids (plasmalogen)

| | |
|---|---|
| • Preparation according to example I | 45.0 g |
| • Ammonium glycyrrhizinate | 12.5 g |
| • Purified water | 10 l | for 1000 ampuls of 10 ml

EXAMPLE VIII

Sachets of drinkable powder based on cerebral phospholipids rich in ether lipids (plasmalogen)

| | |
|---|---|
| • Preparation according to example I | 100.0 g |
| • Magnesium oxide | 500.0 g |
| • Zinc gluconate | 125.0 g |
| • Vitamin E | 30.0 g |

-continued

| | |
|---|---|
| • Maltodextrin with a high absorption capacity | 2.5 g |
| • Diluent q.s. | | for 1000 sachets 5 g

EXAMPLE IX

Injectible suspension based on cerebral phospholipids rich in ether lipids (plasmalogen)

| | |
|---|---|
| • Cerebral phospholiplds | 10 mg |
| • Sodium chloride | 15 mg |
| • PPI water QS | | for 1 ampuls of 5 ml

EXAMPLE X

Ether lipids dosage in mammalians brains extract has been performed by two methods:

A) Bidimensionnal chromatographic method

Firstly, total lipid extraction by the Folch method as it is described by B. Entressangles, in "Manuel des corps gras" (editions Lavoisier-Paris) 1992-P. 1414–1418. Ether lipids are separated from total phospholipids by bidimensionnal chromatography CIH vapors intermediate hydrolysis. The thus hydrolysed ether lipids into corresponding lyoderivatives, separate from diacylated phospholipids during the second dimension course.

B) By NMR spectrometry

Phospholipids are quantified by [31P] NMR spectroscopy using triphenyl phosphate as an internal control. The samples are treated in a special way to obtain lines and a good resolution. The resulting values are % of phospholipids moles in relation to internal standard.

In order to convert % mole into % per weight, the values are multiplied by the corresponding phospholipid molecular weight.

Cholesterol and cerebrosides are quantitatively determined by [1H]NMR spectroscopy while by adding internal corresponding standards. Ethers lipids data are obtained from signals included in the three spectra. Free fatty acids data are calculated from the [13C] NMR spectrum. Additionally to [31P] NMR measurements, [1H] NMR spectra and and a [13C] NMR spectrum have been carried out. Cholesterol and cerebrosides are added as a standard in order to obtain quantitative values for these two lipids types through the [1H] NMR spectrum. By using the [13C] NMR spectrum, free acids and alkenyl ethers content, can be calculated. Table 2 shows the values obtained on cerebral phospholipids.

| | | |
|---|---|---|
| Total phospholipids | 53.6% | |
| PC-Ether | | 0.7% |
| PE-Ether | | 12.0% |
| Cholesterol | 7.0% | |
| Cerebrosides | 9.0% | |
| Free fatty acids | 5.0% | |
| Total | 74.6% | |

PC-Ether = phosphatidylcholine ether
PE-Ether = phosphatidylethanolamine ether

EXAMPLE XI

Lipids ethers preparations from pig cerebral tissues

Cerebral phospholipids according to this invention are obtained by extracting pig brains removed from freshly slaughtered animals according to the following methods:

- pig brains are removed from freshly slaughtered animals stemming from breedings without any infectious diseases and rigorously followed by veterinary services for the sanitary conditions.
- brains are immediately frozen at −20° C. and kept at this temperature
- brains are then reduced to a temperature comprised between −5° to 0° C. before getting through an industrial mincer and grinders, in order to obtain a liquid paste the content of water of which, is about 80%.
- the brain paste is transferred to the top of an atomizing room wherein water is immediately evaporated through a hot air flow at 190°/195° C.
- the resulting powder is fed into a reactor which contains a mixture of aliphatic hydrocarbons based on hexane and kept under stirring.
- after filtration, the liquid phase is vacuum-concentrated and give rise to a crude extract
- the crude extract is then run into acetone in the presence of an alimentary antioxidising agent
- the obtained precipitate is filtered under nitrogen pressure
- the collected product is vacuum-dried and contains the purified cerebral phospholipids.

EXAMPLE XII

Pharmacological effect demonstration of the preparations according to this invention.

A plasmalogen-rich (phosphoglycero ethers) cerebral phospholipids preparation has been used as a protective agent in a certain number of animal tests.

a) On pyrithiamin-induced experimental neuritis

Pyrithiamin is an antimetabolite which at a 5 mg/Kg IP dose, induces in the mice a tetanic hyperpolarization.

Phospholipids protective activity was tested, on the one hand as a preventive treatment i.e. administered at the same time than pyrithiamin and, on the other hand, as a curative agent, that is when the first neurological symptoms appear.

Results are reported Table 3 below.

It is stated that the protective activity during preventive treatment is total until doses as low as 2.5 mg of phospholipids per 10 g of food. Knowing that a 20 g mouse eats about 3 g of food a day, the effective dose is about 0.35 mg of phospholipids rich in plasmalogens according to the invention, per animal.

TABLE 3

| Dosis of phospholipids in 10 g food in the groups under experiment | Preventive effect | | Curative effect | |
|---|---|---|---|---|
| | Controls | Experim. | Controls | Experim. |
| 10 mg | +++ | 0 | +++ | + |
| 5 mg | +++ | 0 | +++ | ++ |
| 2,5 mg | +++ | 0 | +++ | ++ |
| 2 mg | +++ | + | +++ | ++ |
| 1 mg | +++ | +++ | +++ | +++ |

+++Acute polyneuritis: al animals die in few days
++Attenuated symptoms: survival of more than 50% of animals
+light symptoms: all animals survive
0 no symptom b) Protective effect of phospholipids rich in plasmalogen on oxotremorine-induced neurological symptoms Oxotremorine induces in the mice very characteristic static tremblings, of the Parkinson's disease type, as well as peripheral symptoms such as lachrymation and salivation.

TABLE 4

| Dosis of phospholipids in 10 g food in the groups under experiment | Duration of the treatment with phospholipids before tremorine | Intensity of the symptoms as a function of time after arrest of the treatment | | | |
|---|---|---|---|---|---|
| | | 1 j | 2 j | 3 j | 4 j |
| 0 mg | | +++ | +++ | | |
| 50 mg | 3 days | 0 | 0 | ++ | |
| 30 mg | 3 days | 0 | 0 | ++ | |
| 20 mg | 3 days | 0 | ++ | +++ | |
| 10 mg | 3 days | 0 | +++ | | |
| 0 mg | | +++ | +++ | | |
| 50 mg | 1 days | 0 | 0 | +++ | |
| 30 mg | 1 days | 0 | 0 | +++ | |
| 20 mg | 1 days | 0 | +++ | | |
| 10 mg | 1 days | 0 | +++ | | |

Table 4 clearly shows that 50 mg of phospholipids per 10 g of food administered during 3 days before oxotremorine injection, completely inhibit symptoms appearance (tremblings), this inhibition to the oxotremorine action lasts 3 days.

c) Effects of phospholipids rich in plasmalogens on experimental allergic encephalomyelitis An encephalomyelitis is induced among 20 rats by injecting a spinal chord suspension (Freund's adjuvant). Disease grows up from the 10th to the 14th day. These animals divided into 3 groups have been treated every day with increasing dosis of phospholipids.

TABLE 5

| Dosis of brain phospholipids I.M | Lack of symptoms | | | Not cured |
|---|---|---|---|---|
| | after 7 j | after 14 j | after 21 j | |
| 0,01 mg | 1 | 2 | 1 | 16 |
| 0,02 mg | 8 | 17 | | 3 |
| 0,5 mg | 6 | 18 | | 2 |

The curative effect is thus very clear.

EXAMPLE XIII

Clinical effect demonstration of preparations according to this invention

A clinical trial have been undertaken with a group of children suffering from severe mental handicaps. One treated group of 104 children has been compared to an untreated group of 85 children aged from 1 to 14. Treatment consists in a 30 mg phospholipids supply a day per os for 6 to 12 months periods as the case may be. Psychometric tests, I.Q. measurements or electroencephalographic recording have been achieved according to the age or the symptomatology.

It will be noted in Table 6 below, that more of six children out of ten, have gained an important benefit from this treatment.

TABLE 6

| | RESULTS TREATED CHILDREN | | | | RESULTS UNTREATED CHILDREN | | | | |
|---|---|---|---|---|---|---|---|---|---|
| | Number | None | Weak | Significant | Very marked | Number | None | Weak | Significant | Very marked |
| DOWN'S syndrom | 40 | 0 | 13 | 21 | 6 | 24 | 6 | 15 | 3 | 0 |
| LITTLE'S disease | 22 | 6 | 6 | 8 | 2 | 11 | 9 | 2 | 0 | 0 |
| Post meningo-encephalitic condition | 7 | 0 | 3 | 4 | 0 | 7 | 5 | 2 | 0 | 0 |
| Post ictero-nuclear condition | 9 | 0 | 3 | 4 | 2 | 5 | 4 | 1 | 0 | 0 |
| Endogenous debility | 13 | 2 | 2 | 6 | 3 | 18 | 11 | 7 | 0 | 0 |
| Petit mal | 4 | 0 | 0 | 3 | 1 | 6 | 3 | 2 | 1 | 0 |
| Grand mal | 9 | 1 | 2 | 4 | 2 | 10 | 6 | 3 | 1 | 0 |
| TOTAL | 104 | 9 8,6% | 29 27,8% | 50 48% | 16 15,3% 63,3% | 81 | 44 42,3% | 32 30;7% | 5 4,8% | 0 |

I claim:

1. A composition for treating neurodegenerative diseases comprising an anti-neurodegeneratively effective amount of glycerated phospholipids from mammalian brains or fish containing 5 to 25% by weight of a compound

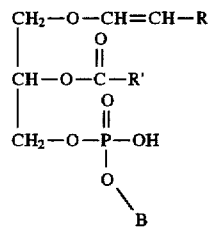
                I wherein R is alkenyl of 10 to 24 carbon atoms containing 1 to 5 double bonds, R' is alkenyl of 10 to 24 carbon atoms containing 1 to 6 double bonds and B is selected from the group consisting of choline, ethanolamine, serine and inositol and an inert pharmaceutical carrier.

2. The composition of claim 1 containing 10 to 15% by weight of the compounds.

3. The composition of claim 1 further containing at least one member selected from the group consisting of vitamins $B_1$, $B_2$ and $B_6$, vitamin PP and folic acid.

4. The compound of claim 1 further containing at least one magnesium salt.

5. The composition of claim 1 further containing at least one trace element selected from the group consisting of selenium, lithium and rubidium.

6. The method of treating neurodegenerative diseases in humans administering to humans in need thereof an antineurodegeneratively effective amount of glycerated phospholipids from mammalian brains or fish containing 5 to 25% by weight of a compound of Formula

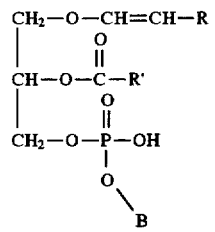
                I wherein R is alkenyl of 10 to 24 carbon atoms containing 1 to 5 double bonds, R' is alkenyl of 10 to 24 carbon atoms containing 1 to 6 double bonds and B is selected from the group consisting of choline, ethanolamine, serine and inositol.

7. The method of claim 6 wherein the glycerated phospholipids also contain at least one member selected from the group consisting of vitamins $B_1$, $B_2$ and $B_6$, vitamin PP and folic acid.

* * * * *